(12) United States Patent
Kamøy

(10) Patent No.: US 7,740,018 B1
(45) Date of Patent: Jun. 22, 2010

(54) NON-INVASIVE LASER TREATMENT OF LARGE VARICES

(76) Inventor: Marit Johanne Aoude Kamøy, Camilla Collets Vei, 0258 Oslo (NO)

( * ) Notice: Subject to any disclaimer, the term of this patent is extended or adjusted under 35 U.S.C. 154(b) by 1132 days.

(21) Appl. No.: 11/287,684

(22) Filed: Nov. 28, 2005

Related U.S. Application Data

(60) Provisional application No. 60/631,185, filed on Nov. 29, 2004.

(51) Int. Cl.
*A61B 19/00* (2006.01)
(52) U.S. Cl. .......................... 128/898; 607/88; 607/89; 606/3; 606/9
(58) Field of Classification Search .............. 128/898; 607/88–92; 606/3, 9
See application file for complete search history.

(56) References Cited

U.S. PATENT DOCUMENTS

| | | | |
|---|---|---|---|
| 5,758,665 A * | 6/1998 | Suval .......................... 128/898 |
| 6,027,495 A | 2/2000 | Miller | |
| 6,096,029 A | 8/2000 | O'Donnell, Jr. | |
| 6,214,034 B1 | 4/2001 | Azar | |
| 6,306,130 B1 * | 10/2001 | Anderson et al. ............. 606/27 |
| 6,398,777 B1 * | 6/2002 | Navarro et al. ................. 606/7 |
| 6,986,766 B2 * | 1/2006 | Caldera et al. ................ 606/15 |
| 2006/0217692 A1 * | 9/2006 | Neuberger .................... 606/12 |
| 2007/0016072 A1 * | 1/2007 | Grunwald et al. ........... 600/468 |
| 2007/0100328 A1 * | 5/2007 | Cohen .......................... 606/12 |

FOREIGN PATENT DOCUMENTS

WO    WO 02/064209 A1    8/2002

OTHER PUBLICATIONS

"Effective Treatment of Deep and Large Vessels with VascuLight™," PhotoDerm® Application Notes. 1(6):1-4. ESC Medical Systems Ltd. (1998).
Moraga et al. "European Multi-Center Study: PhotoDerm® VascuLight™ for the Treatment of Varicose Reticular Veins and Leg Telangiectasias, as well as Other Vascular Lesions." Clinical Application Notes. 8(1):1-6. ESC Medical Systems Ltd. (1999).

* cited by examiner

*Primary Examiner*—Ahmed M Farah
(74) *Attorney, Agent, or Firm*—Knobbe Martens Olson & Bear LLP

(57) ABSTRACT

The invention is directed to a method, a laser system, and a kit for non-invasive treatment and removal of varices. In particular the invention allows for non-invasive laser treatment of large varices, such as varices having a diameter larger than 5 mm. The method of treatment can apply presently available dermatological lasers. The invention further propose developments and additions to presently available dermatological lasers making these particularly applicable to the treatment method.

10 Claims, 3 Drawing Sheets

NON-INVASIVE LASER TREATMENT OF LARGE VARICES

CROSS-REFERENCE TO RELATED APPLICATIONS

The present application claims the benefit of priority to U.S. Provisional Patent Application Ser. No. 60/631,185, filed Nov. 29, 2004, the disclosure of which is hereby expressly incorporated by reference in its entirety.

FIELD OF THE INVENTION

The present invention is directed to a method, a laser system, and a kit for non-invasive treatment and removal of varices, in particular large varices.

BACKGROUND

Dermatological treatment methods for treating a range of abnormalities in both the epidermis and the dermis of the human body are well known in the art. Such abnormalities can be e.g. birthmarks, port-wine stains, spider veins, varicose veins (varices) or other.

Varicose veins are dilated (expanded) distended veins that lie just under the epidermis of the skin. This condition occurs in about 15% of the population, and is seen most commonly in women who have been pregnant, but it is known to occur as early as by the age of 14-15 years.

The medical term for varicose veins is varices or venous insufficiency. The key function of the venous system is to transport deoxygenated blood from the various organs and parts of the body back to the heart. In normal functioning veins, valves located within the veins prevent the venous blood from returning back down to the leg. When these valves no longer function correctly the vein is termed 'incompetent' and venous blood collects in the veins, which causes them to dilate.

The result is visible outpouching varices or varicose veins that cause pain, swelling and discomfort in the lower limbs as well as long term effects such as reduced venous circulation leading to premature aging of the skin. These are indications of a malfunction in the venous system and should be investigated in order to initiate possible treatment.

The most commonly applied treatment for treating small and relatively uncomplicated varices is simple compression therapy. By compression therapy the patient is instructed to wear compression/elastic stockings or bandages for shorter or longer periods of time, until the varices are reduced or wholly treated due to increased blood circulation in the tissue. In addition to this, the patient is also typically instructed to keep the relevant limbs in a raised position when resting, in order to ease the backflow of deoxygenated blood.

In particular in relation to varicose veins, use of laser light irradiation applied to the skin of a living human is a widespread and broadly recognized treatment method, albeit such a method is regarded possible only for the treatment of smaller sized veins having a cross-section diameter in the range of 0-5 mm.

U.S. Pat. No. 6,027,495 to Miller relates to a method and apparatus for dermatological treatment used for removing vascular and pigmented lesions from the skin of a living human. The method is carried out by using a modified high power diode laser system under carefully controlled conditions. From this document, one is taught that such a treatment by laser light irradiation yields the best results on varicose veins (vessels) in the range of 0.1-3.0 mm (cf. column 11, line 7-10).

A description of state of the art non-invasive laser treatment of varices may be found in "Effective Treatment of Deep and Large Vessels with VascuLight™", PhotoDerm® Application Notes, Volume 1, Number 6, ESC Medical Systems Ltd, 1998 (www.aesthetic.lumenis.com/pdf/treatment_of_deep.pdf), or in Moraga et al., Clinical Application Notes Vol. 8 No. 1, ESC Medical Systems, 1999 (www.aesthetic.lumenis.com/pdf/european_multicenter.pdf).

Treatment of larger sized varicose veins, i.e. having a cross-section diameter above 5-8 mm, typically relies on invasive methods. Such invasive methods can comprise of e.g. removal by surgery such as avulsion phlebectomy (removing the whole or part of the vein) which is also known as 'stripping', sclerotherapy (injecting an agent that obliterates the vein) or laser ablation such as endoveneous laser therapy (EVLT).

EVLT treatment involves destruction of the venous tissues by means of heat. Laser energy from a diode laser is delivered inside a vein by using an optical fiber inserted in the vein through an small incision. The laser energy closes the vein from the inside as the laser fiber is pulled through a small cannula drawn through the vein. When the diode laser is triggered, it deposits thermal energy in the blood and the venous tissues, thereby causing irreversible venous tissue damage in the irradiated area. The laser is fired repeatedly as the laser fiber is carefully and stepwise drawn through the vein until it is treated. Although a hole may turn up in the vessel wall where the laser beam makes contact with it, permanent ablation of the vein happens due to the thermal injury to the entire circumference of the vessel.

The disadvantage of the existing methods is the use of surgical methods which require an incision with instruments.

SUMMARY OF THE INVENTION

As can be seen from the above, nothing in the prior art suggests the possibility of treating larger sized varices by non-invasive methods.

It is therefore an object of the current invention to provide a treatment of large varices, which require no incisive actions in the human body by combining the advantages of the invasive methods with those of the non-invasive methods.

In a first aspect, the invention provides a method for non-invasive laser treatment of varices with a diameter larger than 5 mm in a human body, the method comprising the steps of, for a varicose vein having a diameter larger than 5 mm, establishing increased blood pressure and reduced blood circulation in the varicose vein; and irradiating the varicose vein with a pulsed coherent light from outside the human body while requiring no incisive actions.

As previously mentioned, in the present context, the term varicose vein refers to the section of a vein, which is dilated (expanded). While the non-invasive treatments according to the prior art are only used to treat varices with a diameter smaller than 3 mm, the present invention allows treatment of varices with a diameter larger than 5 mm. Clinical tests have shown that even varices larger than 6 mm, such as larger than 7 mm or 8 mm, such as larger than 9 mm or 10 mm, furthermore even larger than 12 mm can be successfully treated with the invention. In the present context, the diameter of a varice or a varicose vein is the cross-sectional diameter of the undisturbed vein in a plane normal to the direction of blood flow.

The pulsed coherent light is typically provided by a pulsed laser capable of performing selective photothermolysis, preferably a laser for dermatological laser treatment. A large number of dermatological lasers on the market may be applicable for the method according to the invention.

By way of experiments, it has been found that the main decisive parameters leading to the successful treatment of larger sized veins are, beside the laser parameters, the reduction of blood circulation as well as increase of blood pressure in the treated veins.

When the irradiation is performed, the semifluent content of the distended varicose vein accumulates heat and transmits heat to its closest surroundings, i.e. the vessel wall. The vessel wall which mainly consists of heat-unstable proteins, will undergo a denaturation in which the structural composition of proteins changes and the original feature of the vessel is destroyed and disappears.

When reducing the blood circulation in the veins to be treated, a more efficient heating of the wall of the distended vessel may be obtained. It is mainly water contained in the blood that absorbs radiation energy. Hence, if there is a large flow of blood through the vein, both the heating of the blood and the heat transfer from the blood to the vessel wall becomes less efficient. Reducing the blood circulation will increase the amount of heat transferred to the vessel wall without the need for increasing the radiation. Since an increase in the amount of heat energy that reaches and is absorbed by the vessel wall is found to be important in regard to the efficiency of the treatment, a reduction in blood circulation is a relatively simple way of improving the treatment.

Also, an increase in blood pressure in the veins to be treated has proven to make the treatment more efficient. When increasing the blood pressure in the varicose veins, the varices have a tendency to protrude more from the surface of the skin, which makes them easier to find. This may further render the need for applying pressure on the skin when applying the irradiation redundant, since the varices are protruding and therefore visible to a higher degree than normal, which in turn may lead to a more efficient and correctly targeted application of the irradiation.

In non-invasive treatment of smaller varices according to the prior art, it has been taught that a mild pressure was applied to the varicose vein with the laser application handpiece upon irradiation. This served to create a better optical contact between handpiece and the skin as well as to compress the vein. In developing the method according to the invention, it was found that the efficiency of the treatment were considerably improved by not compressing the varicose vein during light application. By avoiding pressure, one increases the amount of heat-absorbing colored blood cells (hemoglobin) in the varicose vein, and thereby increases the amount of absorbing matter. Avoiding pressure application also keeps the treated vessel maximum dilated and exposed to treatment, whereby the tissue is distended and stretched. Distended and stretched tissue constitutes a thinner layer which thereby has less specific heat capacity, leading to a faster heating by the adjacent blood. Therefore the method preferably comprises keeping the varicose vein at least substantially uncompressed during light application.

The reduction in blood circulation as well as the increase in blood pressure in the veins to be treated is preferably established by keeping the human body in an upright, standing position during the treatment. Alternatively, keeping the human body in an almost vertical reclined position may give substantially the same effect and is also considered within the scope of the present invention. The increased effect is linked to the fact that varices are normally located in the legs, so that gravity ensures the desired effect when the patient is standing upright. Hence, the method of treatment is preferably applied to varices located in the lower limbs such as in the legs or ankles.

Alternatively, the increased blood pressure and reduced circulation may also be obtained by applying pressure to the varicose vein above/downstream from the varix.

The selective photothermolysis of the method according to the first aspect is preferably performed with a laser wavelength in the near-infrared regime having large absorption in water and a lower absorption in other main tissue components (hemoglobin, oxyhemoglobin, melanin). In a preferred embodiment, the laser wavelength is chosen in the near-infrared regime, such as in the interval 800-1200 nm or in the interval 950-1100 nm. Preferably, the laser is a Nd:YAG laser having a wavelength of 1064 nm.

In order to be able to apply the light in an efficient manner, a shape and size of the beam profile (also referred to as the spot) of the applied light compares to the treatment area of the varicose vein. As the dilated section of the vein is typically longer than the diameter of the dilation, the treatment area is in general elongated. Applying a laser spot shaped like a varice has not been applied in the prior art. Previous dermatological lasers have typical spot sizes between 3-6 mm. Systems used to cover larger skin areas typically scans a smaller spot size over the area.

It would be advantageous if a laser system for selective photothermolysis on large varices be provided. The laser system should preferably comprise:
   a pulsed laser for generating near-infrared light pulses;
   a light guide optically coupled to the laser to receive and guide light from the laser;
   a dermatology handpiece connected to receive light from the light guide and emit light from an application head;
   control circuitry electronically connected to the laser and controlling generation of pulses of light in the laser;
   wherein the dermatology handpiece comprises optical components providing for the emitting of a light beam with an elongated beam profile having a length, L, in the range of 12-60 mm and a width, W, in the range of 4-20 mm and an aspect ratio W/L, in the range of ½-⅐.

Preferably, the elongated beam profile is oval or rectangular with rounded corners. The beam profile may be formed by shaping the beam with lenses, mirrors and other optical components, in particular cylindrical lenses. Alternatively, the beam profile is defined by an aperture. When determining dimensions of the beam profile, only areas having a significant intensity or fluency should be considered.

Providing a beam diameter shaped and dimensioned like the varices allows for a much more efficient treatment. More energy can be delivered in a shorter time without burning of the skin—hence heating of the vessel wall become faster.

As varices of different sizes are typically encountered during the same treatment session, it would be preferable to be able to adjust the spot size to correspond to the dilated section of each individual varicose vein.

Hence, in a second aspect, the invention provides a laser system for selective photothermolysis on large varices. The laser system comprises:
   a pulsed laser for generating near-infrared light pulses;
   a light guide optically coupled to the laser to receive and guide light from the laser;
   a dermatology handpiece connected to receive light from the light guide and emit a light beam from an application head;
   control circuitry electronically connected to the laser and controlling generation of pulses of light in the laser;

wherein the dermatology handpiece comprise optical components for adjusting a cross sectional area of the light beam allowing the operator to accurately adjust an illuminated area to the size of a varice.

Whereas the second aspect relates to the shape of the emitted beam, the second aspect provides the possibility of adjustment of the size of the emitted beam, independently of the shape.

Increasing the cross sectional area of the light beam allows for an increase in the pulse energy without burning of skin as the energy becomes distributed over a larger area. In a preferred embodiment, the pulse fluency (energy per area per pulse) is kept around some predetermined level where burning of the skin is not prominent—typical values are in the range of 140-180 J/cm$^2$. To do this, the control circuitry of the laser system preferably comprise means for, upon adjustment of the area of the light beam, adjusting a pulse energy proportionally to the area of the beam profile, to maintain an at least substantially constant fluency of the pulse. The pulse energy may be adjusted by adjusting either the laser power or the pulse duration or both.

The method according to the first aspect may be performed using a dermatological laser apparatus according to the prior art or a laser system for selective photothermolysis according to the second aspect. However, users of these prior art apparatuses were taught that they were only suitable for treating smaller sized varices. In the above described method according to the invention, this prejudice is overcome with regard to the use of such systems.

Accordingly, in a third aspect, the invention provides a kit for non-invasive treatment of varices with a diameter larger than 5 mm in a human body, said kit comprising a generation and application part and an instructional part, the generation and application part comprising:

a pulsed laser;

a light guide optically coupled to the laser to receive and guide light from the laser;

a dermatology handpiece connected to receive light from the light guide and emit light from an application head;

control circuitry electronically connected to the laser and controlling generation of pulses of light in the laser, the instructional part comprising of a set of instructions inviting a user to use the generation and application part in treating varices having a diameter larger than 5 mm, the set of instructions further instructing the user to irradiate a varicose vein to be treated with the dermatology handpiece from outside the human body while requiring no incisive actions, and to establish increased blood pressure and reduced blood circulation in the varicose vein.

Preferably, the set of instructions further instruct the user to maintain the dermatology handpiece in contact with skin overlying the varicose vein while maintaining the varicose vein at least substantially uncompressed during light application.

The generation and application part of the kit according to the invention is well known in the art, and different apparatuses comprising such a part and facilitating its use are currently available on the market and will not be described in further detail here.

The instructional part of the kit according to the invention comprises a set of instructions in which a user is invited to treat varices and other vascular lesions such as those mentioned in the Background part of the current application, however conducting such treatment on varices or lesions that may be substantially larger in diameter than previously possible, i.e. larger than 5 mm.

The set of instructions instruct the user to treat the relevant varicose vein by irradiating it from outside the skin of the human body with light emitted from the dermatology handpiece without the requirement of any incisive actions.

In another formulation, the kit according to the third aspect comprises any dermatological laser apparatus with instructions for carrying out the treatment according to the first aspect using the laser.

The dermatology handpiece is preferably connected to the generation part in such a way that it may be moved around freely and positioned anywhere on the skin of the human body being treated. During the treatment, the position of the dermatology handpiece is preferably shifted after each application of a light pulse hereby "attacking" the varicose vein from various and constantly shifting angles. Also, every once in a while between pulses, the user may preferably exert a little pressure with one or more fingers on the varicose vein in order to feel the current state of and/or register any changes in the treated vein.

To palpate an untreated varicose vein may be described as palpating a fluctuation region—that is tissue with a liquid filled cavity located under the skin. After the treatment there is no longer a vessel, merely the remains of the destroyed tissue. This is recognized at the skin surface as a collapse of the protruding vessel and palpating the treated area after treatment reveals an induration (an abnormally hard spot or region of the skin) instead of a fluctuation—while the skin surface is unchanged.

In a preferred embodiment of the kit the set of instructions may comprise any one or more of the following: a manual, a booklet, a video tape, an audio tape, a CD-ROM, a DVD, a floppy disc, a pre-programmed memory device for plug-and-play application (USB), access to online guidance, access to telephone guidance or access to a seminar on the use.

The manual may be a printed handbook supplied in the same packaging in which the generation and application part is delivered. The manual preferably contains technical information concerning the properties and the intended use and maintenance of the apparatus. The manual further contains important directions related to the use of the apparatus. Such directions may tell the user how to apply the apparatus to a given diagnosis, and thereby implicitly state to which diagnoses the apparatus is applicable. In an example, the directions may state that in case of large varices, the user should apply the treatment by carrying out the method according to the present invention, e.g. irradiating the varices when the person to be treated is in an upright, standing position. The printed manual typically also contains drawings or figures in order to facilitate a graphical instruction of the user.

A CD-ROM, DVD or floppy disc may preferably contain the same information and guidance as a printed handbook. However, it may also comprise instruction photographs and/or video sequences for showing the user how to apply the treatment by carrying out the method according to the present invention as described above.

The set of instructions may also preferably comprise possible access to a telephone helpline or to online guidance on a site on the Internet. Here, trained personnel can answer questions and be of assistance in relation to the operation of the apparatus and/or in relation to application of the treatment by carrying out the method according to the present invention as described above.

The set of instructions may also preferably comprise an invitation to a seminar or one or a number of training lessons held by trained personnel in order to teach the user how to apply the treatment by carrying out the method according to the present invention as described above.

Other ways or means of constituting the set of instructions may of course be possible and the scope of the current invention is not to be construed limited by way of the above mentioned examples.

The above described method and kit of the current invention provides a number of apparent advantages over the prior art.

Typically, such a treatment will be carried out in private clinics, but may in principle be carried out at any location capable of accommodating the kit. Therefore it is advantageous that the kit of the current invention does not take up too much space or is too heavy. Using the method of treatment according to the invention, it is possible to treat patients having large varices on site (e.g. in a clinic), instead of the time consuming, unpleasant and potentially very costly hospitalization of patients required by prior art treatment for large varices. Such ambulatory treatment is typically more appealing to potential patients than traditional treatment by surgery.

Since there is no need for surgical or incisive actions in connection with the treatment according to the invention anesthetization is also not necessary. Furthermore, the necessity of working in a sterile location (clean room) with sterilized instruments is also avoided by the invention.

In addition this, non-invasive treatment of large varicose veins may be given to patients who are not fit for surgery, such as elderly patients and patients using medication such as anti-coagulants.

Without the need for incisive actions as well as anesthetization there is practically no health risk involved with the treatment according to the present invention. Furthermore, no scars will appear from such actions. A few minor side effects such as swelling or bruising of the treated area or small blisters on the surface of the skin may occur. Enabling physicians and other practitioners to treat larger sized varices with the method and kit according to the invention is therefore most advantageous compared to the prior art. In fact, as described in the Background, the prior art teaches away from the method of the current invention.

In yet another aspect, the invention provides a laser system with a lightweight dermatological handpiece. Users treating many patients may apply several thousand pulses during a single day. Continuously re-positioning and firing the handpiece puts serious strain on the arm, shoulder and back of the user. In most prior art handpieces, the trigger is integrated in the handpiece which thereby also includes electronic circuitry. In a preferred embodiment, the trigger functionality resides in a foot pedal so that no circuitry is needed in the handpiece.

DETAILED DESCRIPTION OF THE INVENTION

Figure 1:
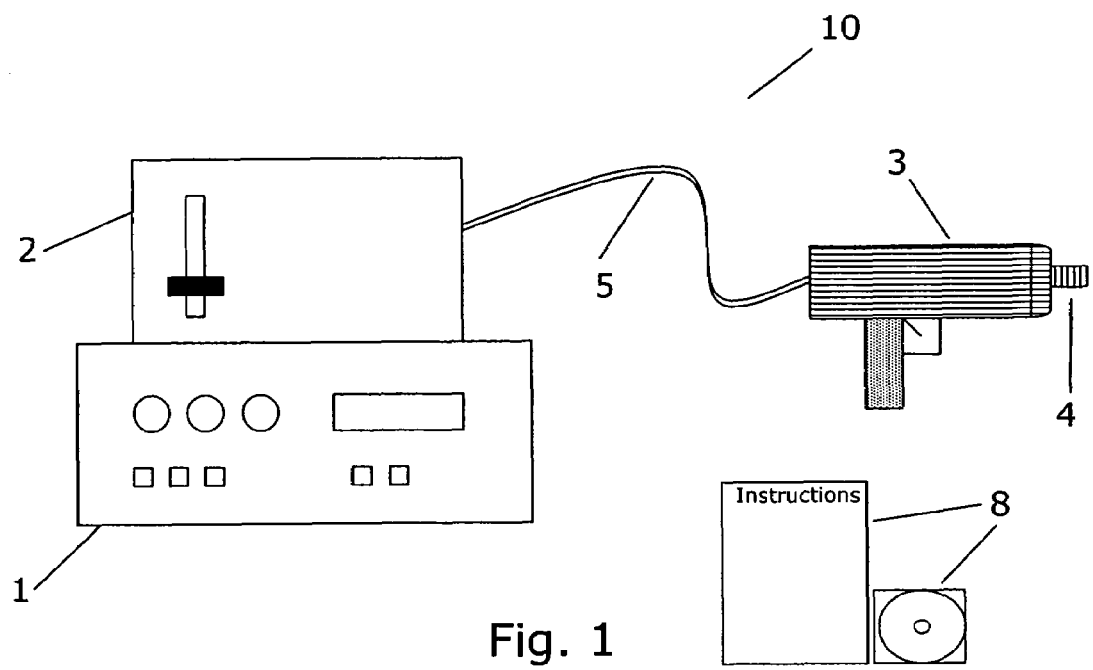
FIG. 1 shows a schematic front view of a kit according to the invention.

FIG. 1 offers a schematic illustration of the treatment kit according to the invention. The generation and application part 10 comprises control circuitry 1 that is electronically connected to a laser 2, wherein the circuitry controls generation of pulses of light in the laser and further allows choosing between the different preprogrammed running modes. The laser 2 also comprises a potentiometer for varying the fluency of the laser light.

The laser 2 is optically connected to a dermatology handpiece 3 via a light guide 5 and during the treatment, the laser light pulses are emitted through an application head 4 positioned on one end of the handpiece 3. The kit 10 also comprises a set of instructions 8 for guiding the user to use the kit in a way according to the invention, e.g. a printed manual or a CD-ROM.

From the dermatology handpiece 3 of the kit a beam of laser light with a wavelength of e.g. 1064 nm can be emitted through the application head 4. This wavelength yields a heating effect penetrating several millimeters into the human body, thereby facilitating treatment of the varices below the surface of the skin without any incisive actions.

Figure 2:
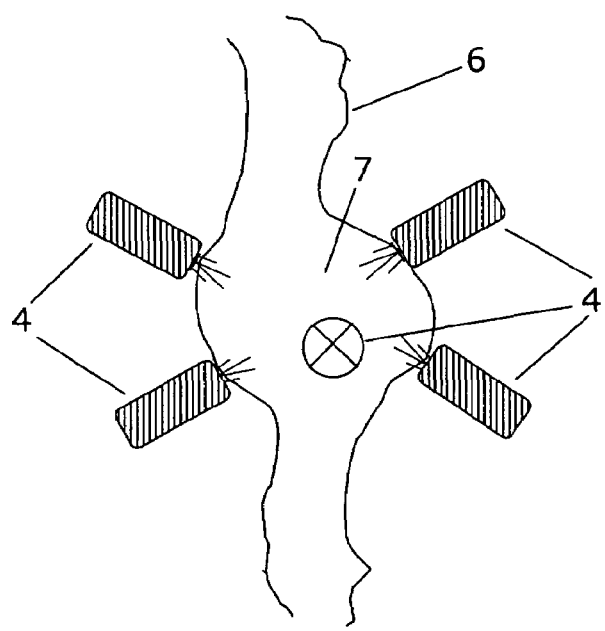
FIG. 2 shows an enlarged, schematic plan view of a varicose vein as well as different angular positions of the dermatology handpiece (not shown in full).

FIG. 2 is a schematic drawing of a varicose vein receiving treatment according to the method of the invention. The valves of a vein 6 have ceased to function correctly so that they no longer prevent the venous blood from returning back down to the limb. This causes the venous blood to collect in the vein leading to dilation, i.e. a varicose vein or varix 7.

By positioning the patient in a substantially upright, standing position during the application of the laser light, as shown in FIG. 2, the user can apply an increased number of light pulses to the same varix 7 from the application head 4. Since the varix 7 will be distended as a result of the patient standing up, the actual area of the skin overlying the varix is increased thereby allowing more applications of light pulses to the same varix before the skin sustains unpleasant burns. This is particularly important since it typically is the risk of serious burns to the skin that limits the number of pulses. This is also illustrated by schematically depicting different angular positions of the application head 4.

Figure 3:
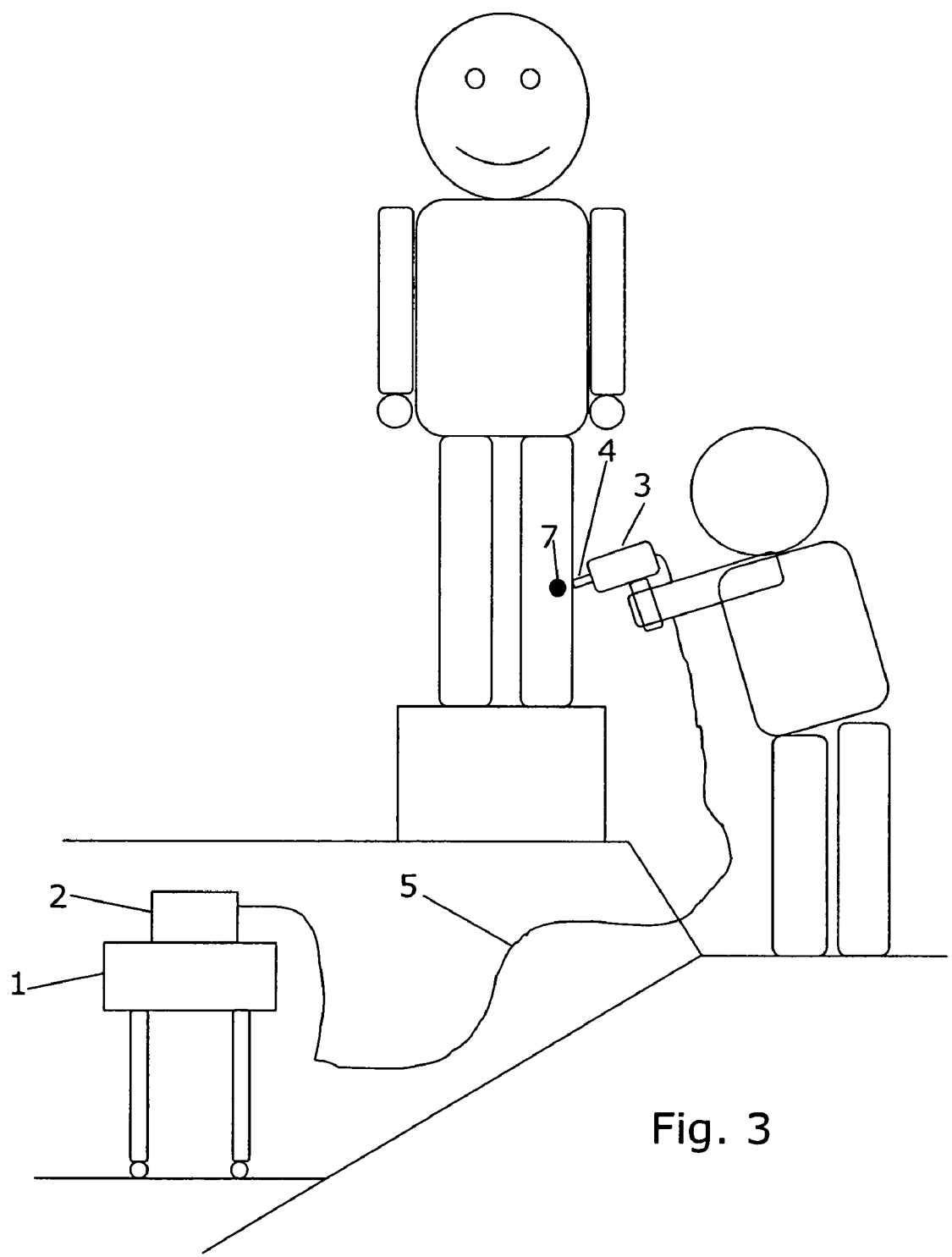
FIG. 3 shows a schematic front view of a typical way of applying the treatment according to the method of the invention.

FIG. 3 is a schematic drawing of a typical treatment situation according to the invention. A user applies treatment to a patient positioned in an upright, standing position by use of the kit according to the invention.

Below a table is shown displaying suggested procedures, settings as well as checking steps in the treatment method. The proposed settings/steps are based on the results of the clinical tests using a Lumenis IPL Quantum DL. The Quantum DL use a Nd:YAG laser and emits at 1064 nm. During testing the apparatus was running in various preprogrammed modes entitled 'Program nos. 1-3' while manually setting the fluency value to 130-150 J/cm$^2$. From 30 to 800 pulses were applied per treatment depending on the amount and size of varices.

The treatment must of course be thoroughly planned for each person receiving treatment taking into consideration the actual size of the varix to be treated. Since individual conditions (skin pigmentation, skin diseases, response to heat etc.) play a role in the response to the treatment, these condition should be taken into consideration as well. The table is therefore primarily a quick overview of the correlation between important patient variables and the applied treatment.

By indicating that varicose veins with a diameter larger than 5 mm can be treated by non-invasive treatment, the table also represents possible content of a set of instructions for inviting a user to apply the method according to the invention in treating large varices. Such table can be provided in a manual for a dermatological laser applicable in the present invention.

| | Program | Fluency [J/cm²] | Check-signs/ things to avoid |
|---|---|---|---|
| Quality of the skin: | | | |
| Soft + pale | 1-2 | 150 | Twisting of the skin |
| Tanned | 3 | 150 | Twisting of the skin |
| Increased tightness in the tissue of the treated limb | 3 | 135-140 | Edema in connective tissue surrounding treated vessel. Jelly-like appearance of the skin |
| Varices located at knee hollow/ankle | 3 | 130-140 | Subcutaneous hematomas White spots Twisting of skin surface |
| Vessel size 3-5 mm | 3 | 110-130 | Subcutaneous hematomas White spots |
| Vessel size 5-12 mm | 2 | 140-150 | Twisting of skin surface |
| Vessel size > 12 mm | 1 | 150 (+) | Heating of the skin |
| Configuration of varices; | | | |
| Cord (string) | 1-2 | 150 | White spots, twisting. |
| Cluster (circle) | 3 | 140-150 | Heating of the skin |

A. Skin Quality

The quality of the skin may differ substantially between patients. A tanned skin should be treated more gently, so should dry and dehydrated skin often seen in elder patients. Pale, elastic and smooth kind of skin is the easiest to treat successfully. Patients who due to their anamnesis easily get bruises should be treated less aggressively.

B. Skin Tightness

The increased tightness of the skin surface and the underlying connective tissue, seen in particular in adipose women, represents a special challenge. A certain edema in the connective tissue surrounding the treated vessel, due to a normal inflammatory response to the laser-induced injury of the vessel, may in this kind of tissue cause a critical decrease in blood circulation of the untreated tissue. Clinically the condition is recognized by a jelly-like appearance of the skin.

C. Location of Varices

The location of the vessel to be treated influences the treatment setting. Varicose veins located at the hollow of the knee and the ankle require special precautions.

D. Configuration of Varices

The configuration of varices also requires attention. Cords of outpouchings along a vessel can be treated more aggressively while clusters of outpouching vessels in a limited area of the lower limb should be treated repeatedly and less aggressively.

The following is a general step-by-step procedure used in the clinical testing of the treatment method of the invention. This procedure thereby also represents a procedure for applying a typical treatment according to the invention, and can be provided in a manual for a dermatological laser applicable for this treatment.

1. Prepare the patient in an upright, standing position as illustrated in FIG. 3 and apply cooling gel to the areas to be treated.

2. Turn on the kit (10).

3. Select one of the preprogrammed running modes of the kit. Pulse duration in the interval 5-15 ms are typical.

4. Enter the desired value for fluency manually. Fluencies in the interval 100-200 J/cm² are applicable, typically a fluency between 140-180 J/cm² is chosen.

5. Place the application head (4) of the dermatology handpiece (3) in touching relationship with a varix to be treated while applying minimal pressure.

6. Shift between triggering a number of laser pulses and constantly surveying the treated vein by touching and feeling with the fingers together with visual inspection in order to establish the effect on the varix and the conditions of the surrounding area, especially changes in coloration or burns to the skin. Also, make sure that the laser light is applied from constantly shifting positions and/or angles as illustrated in FIG. 2 in order to prevent such skin burns. Change the settings of the kit if detected necessary.

7. By touching and feeling with the fingers, determine the change in texture of the varix. When the treated protruding vessel visually collapses and an induration can be palpated instead of a fluctuation, the treatment is finished. If further treatment is needed, the skin covering the varicose vein should be allowed to rest for some minutes whereupon step 6 is repeated until a satisfactory texture is obtained or until light pulses cannot be applied anymore without harming the skin. Typically, varices of diameter ~10 mm will get around 25 pulses per treatment.

8. Repeat steps 6 and 7 above with respect to the number of varices to be treated and until the treatment is considered adequate for a first time treatment.

The patient will experience a certain swelling and slightly increased temperature of the treated areas from day two till day six after the treatment. There will be significant treatment stains lasting for months after the treatment—changing from red just after the treatment, into greyish/almost black after a couple of hours—and finally into a hyperpigmentation which will fade away after some months.

Depending on the effects of the treatment on the individual varices, the above procedure may be repeated up to three times over a period of six to eight months.

The treatment is preferably followed by telephone consultation with the patient 3-4 days after and 3 weeks after treatment. A clinical examination of the treated areas is recommended 3-4 months after the treatment.

The beam profile or spot shape/size of the light emitted from the application head can be adjusted to correspond with the varicose vein. Because of the larger treatment area when treating large varices, it is advantageous to have a larger spot size from the dermatological handpiece. A larger spot size provides the possibility of delivering more energy per pulse while keeping the fluency at a level which does not harm the skin. The larger spot size therefore has a number of advantages described in the following.

With a constant fluency (energy/area) of the pulse, the delivered energy scales with the area of the spot size. Typical spot sizes are circular and between 2-6 mm (diameter at full-width-half-maximum) which is appropriate for treating smaller varices. When treating varices of e.g. 15 mm in diameter, a much larger spot size can be used without irradiating skin outside the varix. As varices are in general elongated, having an irregular spot shape allows for even larger spot sizes to be used without irradiating skin outside the varix.

Figure 4:
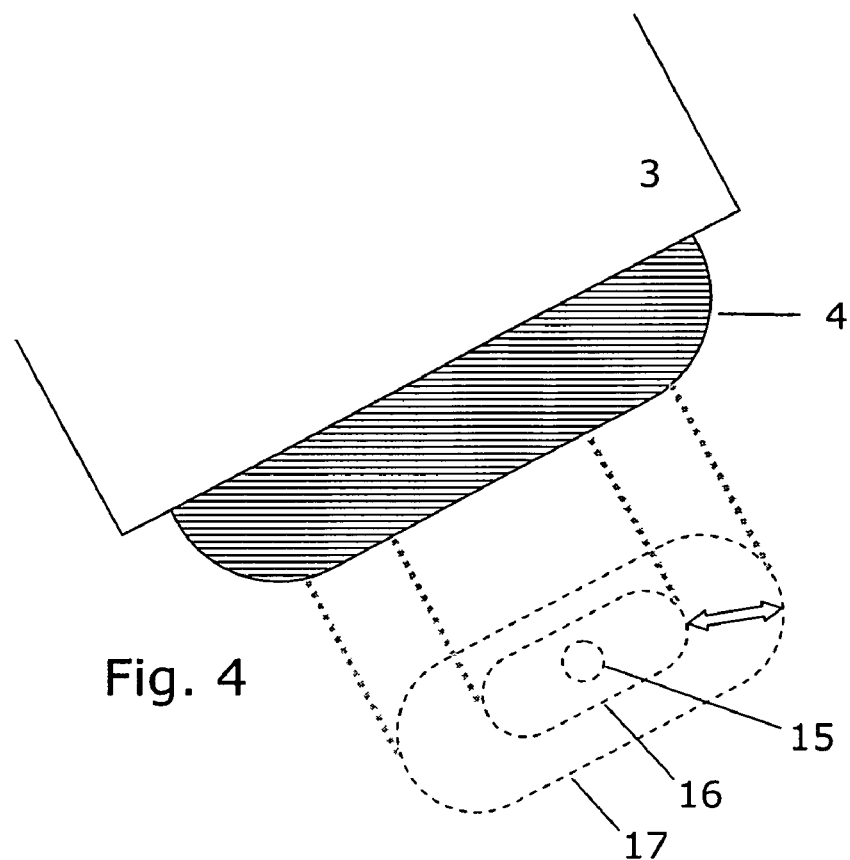
FIG. 4 shows a schematic, perspective/projection view of differently sized and shaped beam profiles emitted from the application head according to the second aspect of the invention.

FIG. 4 illustrates an example. Here, an application head 4 emits a light pulse resulting in a spot (15, 16, 17) on the skin of a patient (the application head is held in contact with the skin—not shown). A circular spot 15 from a pulse with fluency 150 J/cm² and spot diameter 6 mm delivers an amount of energy E=150 J/cm²×π (0.3 cm)²=42 J in a single pulse. A rectangular spot 16 with size 10×20 mm at the same fluency delivers E=150 J/cm²×1 cm×2 cm=300 J in a single pulse. Hence, the energy delivered in a single pulse can be increased by a factor of six without increasing the strain on the skin.

The higher energy delivered by the larger rectangular spot 16 compares to more than six pulses with the smaller circular spot 15. But, the effect caused is far from the same:

Firstly, by applying six pulses, succeeding pulses will typically be overlapped simply because it is not possible exactly to judge the area covered by the preceding pulses. This means that smaller regions of the skin will be burned more than the average, thereby increasing the probability of burns.

Secondly, six pulses will be applied over a much longer time span. A single 300 J pulse may be applied over tens of milliseconds, whereas six 42 J pulses will typically take at least 12-18 seconds. This is because (A) the laser must typically charge between pulses, (B) security measures in the dermatological handpiece does not allow more than one pulses in a given time period, typically, a warning sound of approximately is sounds before each pulse, and (C) the application head must be relocated to another region of the skin covering the varix. During the time span of 12-18 seconds, blood circulation in the varix and heat dissipation to surrounding tissue result in a much lower temperature increase in the target blood and tissue. The much shorter application time of a single pulse has the advantage of substantially increasing the heating of the blood and vein caused by a given amount of applied energy Hence, a single, high energy (same fluency but larger area) pulse provides a much more efficient treatment.

It should be noted that the fluency is not constant over the spot size area. Typically there is a peak in the center according to e.g. a Gaussian beam profile. This means that the above calculations are only approximate.

Figure 5:
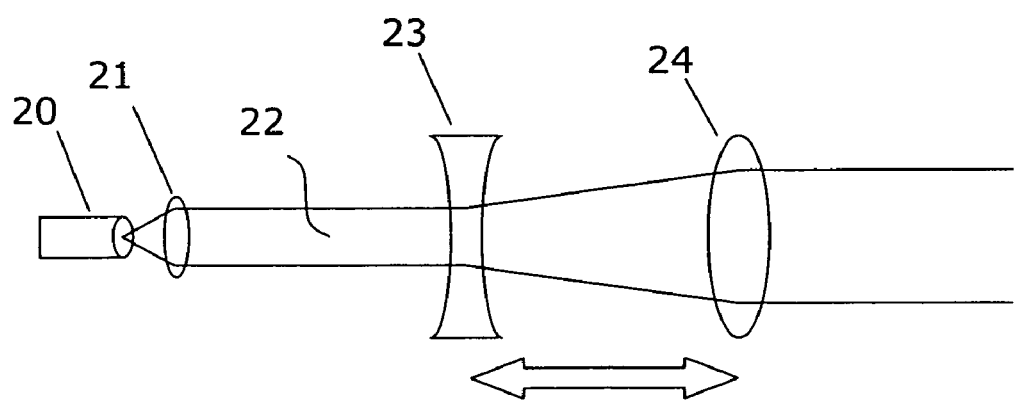
FIG. 5 shows a schematic, perspective view of beam shaping optics in the dermatology handpiece according to the second aspect of the invention.

The spot size may be adjusted by including adjustable beam expanding optics in the handpiece 4 as shown in FIG. 5. This is comparable to the zoom function in a camera, where adjusting the zoom expands/contracts the spot size. In FIG. 5, the end 20 of the light guide emits radiation which is collimated by lens 21. Collimated beam 22 reaches the beam expander consisting of lenses 23 and 24. Adjusting the distance between lenses 23 and 24 will adjust the spot size from spot 16 to 17 in FIG. 4, or vice versa.

Alternatively, the spot size can be adjusted by having several interchangeable application heads, each application head providing for a given spot size depending upon the size of the varix to be treated. This can be enabled by having one or both lenses from the beam expander (lenses 23 and 24) in the application head.

For an oval or rectangular spot shape, the lenses 21, 23 and 24 can be cylindrical or custom made.

In both of the above embodiments, it is important that the total pulse energy is adjusted to obtain a selected fluency, a large spot size requiring larger pulse energy to keep the fluency constant. In a preferred embodiment, the user selects a desired fluency at the beginning of the treatment, typically determined by the skin type of the patient. Before treating a varix, the user adjusts the spot size to fit the size of the varix, and the dermatological handpiece detects the chosen spot size. Based on the current spot size reading from the handpiece, the laser control circuit adjusts the pulse energy, by adjusting the laser power or pulse duration, so that the selected fluency is obtained. If the spot size is adjusted by the user in between pulse applications, the pulse energy is automatically adjusted by the system to give the selected fluency. Existing laser systems can already provide different fluencies while having a fixed spot size—hence, when the user selects fluency, it is the laser pulse energy which is adjusted. Therefore, the preferred embodiment described above requires only modifications to the control system and not to the laser.

The light emitting surface of the application head must increase in size in order to be able to emit larger spot sizes. The outpouching varix creates a skin evagination with a curvature in the range of a radius of the varix. Therefore, if the application head is held so that it does not compress the skin (in accordance with the method of the first aspect), gaps between the skin and the periphery parts of the light emitting surface of the application head will occur. These gaps decrease the efficiency of the treatment by increasing the reflection in the skin. Therefore, in a preferred embodiment, the light emitting surface of the application head is concave, preferably having a curvature radius comparable to the radius of a mid-range sized varix.

What is claimed is:

1. A method for non-invasive laser treatment of a varicose vein that comprises a diameter larger than 5 mm comprising:
   identifying a varicose vein comprising a diameter larger than 5 mm in a human;
   establishing increased blood pressure and reduced blood circulation in the varicose vein while maintaining the varicose vein at least substantially uncompressed;
   irradiating the varicose vein with a pulsed coherent light from outside the human body; and
   maintaining said human in an upright position while irradiating the varicose vein with a pulsed coherent light.

2. The method of claim 1, wherein said human is standing.

3. The method according to claim 1, wherein said varicose vein comprises a diameter larger than 6 mm.

4. The method according to claim 1, wherein said varicose vein comprises a diameter larger than 8 mm.

5. The method according to claim 1, wherein said varicose vein comprises a diameter larger than 10 mm.

6. The method according to claim 1, wherein said varicose vein comprises a diameter larger than 12 mm.

7. The method according to claim 1, wherein said varicose vein comprises a diameter in the range of 5-12 mm and wherein the coherent light pulse comprises a fluency in the range of 140-150 J/cm².

8. The method according to claim 1, wherein said varicose vein comprises a diameter larger than 10 mm and wherein the coherent light pulse comprises a fluency larger than 150 J/cm².

9. The method according to claim 1, wherein the pulsed coherent light comprises a wavelength in the range 950 nm-1100 nm.

10. The method according to claim 1, wherein the pulsed coherent light comprises a wavelength centered at 1064 nm.

* * * * *